United States Patent [19]

Fasnacht et al.

[11] Patent Number: 4,937,524
[45] Date of Patent: Jun. 26, 1990

[54] ROTATING EDDY CURRENT ROLLER HEAD FOR INSPECTING TUBING

[75] Inventors: Floyd A. Fasnacht, Forest; John C. Griffith, Lynchburg; Francis C. Klahn, Huddleston, all of Va.

[73] Assignee: The Babcock & Wilcox Company, New Orleans, La.

[21] Appl. No.: 342,210

[22] Filed: Apr. 24, 1989

[51] Int. Cl.⁵ .............................. G01N 27/90
[52] U.S. Cl. .................... 324/220; 33/544.1; 324/262
[58] Field of Search .................. 324/219–221; 165/11.1, 11.2; 73/623; 33/178 E, 178 F

[56] References Cited

U.S. PATENT DOCUMENTS

| | | | |
|---|---|---|---|
| 2,684,464 | 7/1954 | Hastings et al. | 324/220 |
| 3,443,211 | 5/1969 | Wood et al. | 324/220 X |
| 4,441,078 | 4/1984 | Lecomte | 324/219 |
| 4,550,605 | 11/1985 | Bains | 324/220 X |
| 4,625,165 | 11/1986 | Rothstein | 324/220 |
| 4,675,604 | 6/1987 | Moyer et al. | 324/220 |
| 4,772,849 | 9/1988 | Tedder | 324/220 |
| 4,851,773 | 7/1989 | Rothstein | 324/220 |

*Primary Examiner*—Gerard R. Strecker
*Attorney, Agent, or Firm*—Robert J. Edwards; D. Neil LaHaye

[57] ABSTRACT

A rotating eddy current roller head for inspecting tubing. A main body portion has a set of whisker wheels rotatably attached thereto which center the main body portion in the tube. A roller housing slidably mounted on the main body portion for radial movement relative thereto is caused to track the surface of the tube by opposing magnets mounted in the main body portion and roller housing. An eddy current coil is mounted in a coil holder which is pivotally mounted in an offset manner at the exterior end of the roller housing. A spring mounted in the roller housing biases the trailing edge of the coil holder against the surface of the tube to maintain the eddy current coil at a constant distance from the surface of the tube during inspection procedures.

11 Claims, 2 Drawing Sheets

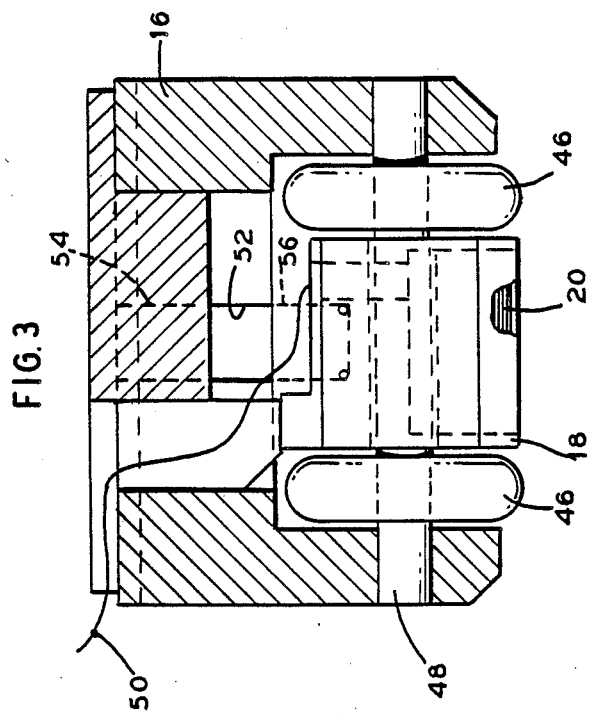
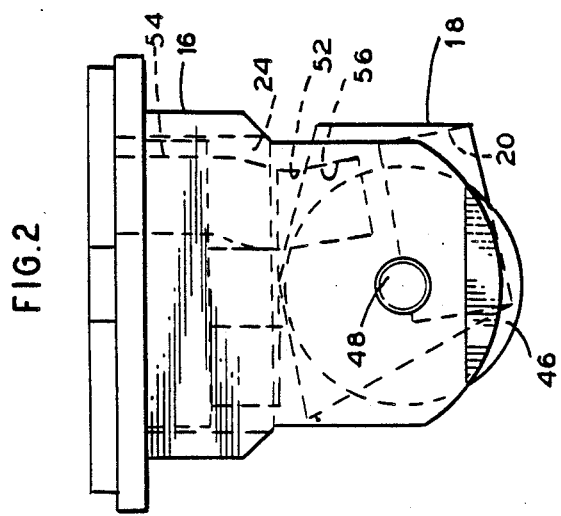

ROTATING EDDY CURRENT ROLLER HEAD FOR INSPECTING TUBING

BACKGROUND OF THE INVENTION

1. Field of the Invention

The invention relates generally to nondestructive testing and in particular to the use of a rotating eddy current probe to inspect steam generator tubes.

2. General Background

Steam generators used in energy production are generally of the straight tube or U-tube design. Coolant from the nuclear reactor travels through the tubes and transfers heat to the secondary coolant in the steam generator. Due to the serious consequences which would result from a tube leak, the tubes are inspected for defects on a routine basis. These routine inspections typically use a bobbin eddy current coil.

Based on the routine exam, an advanced inspection technique carried out by the use of a coil in a rotating eddy current probe inside the tubes may be performed. The probe may be in contact with or near the surface of the tube and is rotated as it moves through the tube. This results in a helical inspection path for the coil. In the preferred method of inspection, the coil must be maintained in continuous close proximity with the tube's inner surface to obtain inspection results which accurately indicate the presence or absence of flaws in the tubing. In addition to problems encountered with surface irregularity, U-tube designs present higher frictional drag in the bent portion of the tube and a cross section which is more oval in shape than round. Devices for detecting defects in tubular members which are known to applicants include the following.

U.S. Pat. No. 4,675,604 discloses a device for detecting defects which includes an electromagnet for magnetizing the internal surface of a tubular member. The electromagnet is radially supported on rollers.

U.S. Pat. No. 2,684,464 discloses a hollow shaft which is mounted on bearing members so as to be rotatable independently of the bearing members. A detector head is mounted to a support member attached to the shaft so as to be in close proximity to the inner bore surface of the tubular member to be inspected.

U.S. Pat. No. 3,443,211 discloses the use of a magnetic inspection device with a non-contacting caliper having no movable parts that is pulled along the surface of the inspected member.

U.S. Pat. No. 3,472,319 discloses an electromagnet carried by a resilient distortable carriage constructed to urge the electromagnet toward the inner wall of the tube.

U.S. Pat. No. 3,091,733 discloses the use of a standardizing magnet and a stationary detector that detects flaws in the structure being examined by magnetic force changes.

U.S. Pat. No. 4,625,165 discloses a rotating head which carries a transversely slidable sensing member. Readings are taken only as the probe is pulled back towards the open end of the tube through which it was inserted.

An inspection device which overcomes the shortcomings in the present art of difficult rotation, difficulty in tracking the curvature of the tube inner surface, and tendency of the inspection coil to rock away from the inner surface of the tube in varying geometry and frictional forces is needed.

SUMMARY OF THE INVENTION

The present invention solves the aforementioned problem in a straightforward manner. What is provided is an eddy current coil held in close proximity to the inside of a tube being inspected by the repulsion of small magnets. The coil holder is freely hinged on a pin which also serves as an axle for two rollers. The coil holder is biased by a spring so that it follows the tube surface angle and maintains the coil axis close to perpendicular to the inner surface of the tube. The entire head rotates in bearings on a set of whisker wheels that serve to keep the head substantially centered in the tube.

BRIEF DESCRIPTION OF THE DRAWINGS

For a further understanding of the nature and objects of the present invention reference should be had to the following description, taken in conjunction with the accompanying drawings, in which like parts are given like reference numerals and, wherein:

FIG. 2 is a side view of the roller housing of the invention.

FIG. 3 is a front view of the roller housing of the invention.

DETAILED DESCRIPTION OF THE PREFERRED EMBODIMENT

Figure 1:
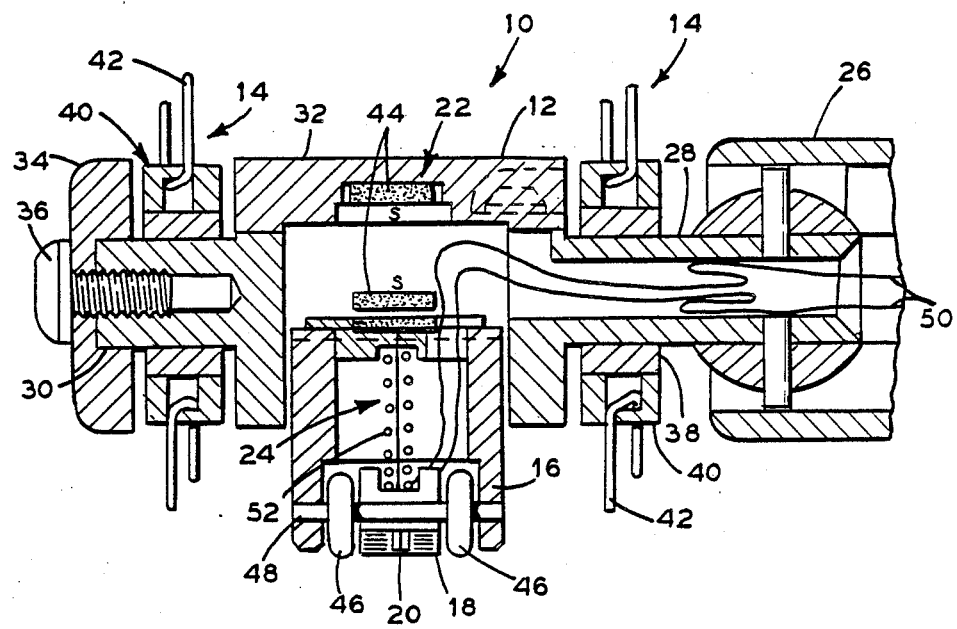
FIG. 1 is a cutaway view of the invention.

Referring to the drawings, it is seen in FIG. 1 that the invention is generally referred to by the numeral 10. Rotating eddy current roller head 10 is generally comprised of main body portion 12, means 14 for centering main body portion 12 in the tube being inspected, roller housing 16, coil holder 18, eddy current coil 20, means 22 for causing roller housing 16 to track the inner surface of the tube being inspected, and means 24 for maintaining eddy current coil 20 at a constant distance from the surface of the tube being inspected.

Main body portion 12 is inserted into the tube to be inspected and rotated by driving tool 26. For ease of illustration only the end of driving tool 26 that connects to the invention is shown as a variety of driving tools are available. Main body portion 12 has first and second ends 28, 30 which are narrower than central portion 32 for the purpose of receiving means 14 for centering main body portion 12. First end 28 is also adapted for driving engagement with driving tool 26. End cap 34 is fastened at second end 30 by any suitable fastening means such as a rivet or bolt 36 and serves to maintain means 14 in position at second end 30.

Means 14 for centering main body portion 12 in the tube being inspected is mounted on the narrowed portions at each end of main body portion 12. Means 14 is formed from whisker wheels comprised of bearings 38, bearing block 40, and U-shaped nylon filament 42. At least two sets of bearings 38 are rotatably mounted on main body portion 12, one on each narrowed portion. A bearing block 40 is attached to each set of bearings 38 and serves as a mounting block for U-shaped nylon filament 42. At least two U-shaped filaments 42 are used at each narrowed portion and extend radially outward substantially opposite each other. U-shaped filaments 42 are sized according to the diameter of the tube being inspected so as to substantially center main body portion 12 therein and are rigid enough to support main body portion 12 in its centered position during inspection operations.

Roller housing 16 is slidably mounted in main body portion 12 for radial movement relative thereto as best seen in FIG. 1. Means 22 for biasing roller housing 16 radially outward from main body portion 12, causing it to track the inner surface of the tube being inspected, is provided in the form of opposing magnets 44. One of magnets 44 is rigidly mounted in main body portion 12 and the other magnet is mounted on the interior end of roller housing 16. The magnets are mounted so that like poles of the magnets face each other. In this manner, the repulsive force generated between the magnets urges roller housing 16 radially outward. Naturally, more than two magnets may be used when the distance between only two magnets would be inadequate to generate the necessary forces. Rollers 46 are rotatably mounted on pin or axle 48 at the exterior end of roller housing 16 such that their axis of rotation is substantially parallel to the longitudinal axis of the tube being inspected. This provides support and minimal resistance as the invention is rotated during the inspection process.

The inspection is carried out by eddy current coil 20 mounted in coil holder 18. Coil 20 illustrated in FIG. 3 is connected by wiring harness 50 to equipment not shown for creating, processing, and recording signals during inspection. Coil holder 18 surrounds coil 20 to prevent damage thereto and is pivotally mounted in an offset fashion on axle 48. Relative to the direction of rotation, coil 20 is mounted at the rear of coil holder 18 as seen in FIG. 2. Means 24 for maintaining coil 20 at a constant distance from the surface of the tube being inspected is in the form of spring 52 mounted in bores 54 and 56 provided in roller housing 16 and coil holder 18 as seen in FIG. 1. Bore 56 is provided adjacent the rear end of coil holder 18. In this manner, pressure from spring 52 causes coil holder 18 to pivot backwards. The rear edge of coil holder 18 rides on the inner surface of the tube being inspected, thus keeping coil 20 at a constant distance from the surface of the tube.

In operation, rotating eddy current roller head 10 is attached to a driving device 26 and inserted into a tube to be inspected. U-shaped filaments 42 position main body portion 12 in substantially the center of the tube while it rotates on bearings 38 in response to rotational torque from driving device 26. Opposing magnets 44 cause roller housing 16 to track the surface of the tube by riding on rollers 46. Pressure from spring 52 causes the rear of coil holder 18 to ride along the surface of the tube, keeping eddy current coil 20 at a constant distance from the surface of the tube. The forces from magnets 44 and spring 52 both serve to keep eddy current coil 20 at the constant proper distance from the tube surface to obtain reliable test results. Electronic equipment known in the industry attached to the end of wiring harness 50 allows eddy current coil 20 to generate and receive signals which are processed by the equipment as the invention is pulled through the tube to determine if any defects are present in the tube. In the preferred embodiment the bulk of the roller head parts are fabricated from Delrin ® for ease of machinability although any material compatible with steam generator systems and possessing reasonable bearing qualities may be used.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

We claim:

1. A rotating eddy current roller head for inspecting tubing, comprising:
   a. a main body portion;
   b. means for centering said main body portion in tubing being inspected;
   c. a roller housing slidably mounted in said main body portion for radial movement relative thereto;
   d. means in said main body portion and said roller housing for biasing said roller housing radially outward from said main body portion, causing said roller housing to track the inner surface of the tube being inspected;
   e. an eddy current coil pivotally mounted at the exterior end of said roller housing on an axis of rotation substantially parallel to the longitudinal axis of said main body portion; and
   f. means in said roller housing for biasing said eddy current coil radially outward, maintaining said eddy current coil at a constant distance from the surface of the tube being inspected.

2. The eddy current roller head of claim 1, further comprising a coil holder which surrounds said eddy current coil.

3. The eddy current roller head of claim 1, wherein said means for centering said main body portion comprises whisker wheels rotatably mounted thereon.

4. The eddy current roller head of claim 1, wherein said means for causing said roller housing to track the inner surface of the tubing comprises opposing magnets mounted in said main body portion and said roller housing.

5. A rotating eddy current roller head for inspecting tubing, comprising:
   a. a main body portion;
   b. means for centering said main body portion in tubing being inspected;
   c. a roller housing slidably mounted in said body portion for radial movement relative thereto;
   d. means in said main body portion and roller housing for biasing said roller housing radially outward from said main body portion, causing said roller housing to track the inner surface of the tube being inspected;
   e. a coil holder pivotally mounted at the exterior end of said roller housing on an axis of rotation substantially parallel to the longitudinal axis of said main body portion;
   f. an eddy current coil mounted in said coil holder; and
   g. means in said roller housing for maintaining said eddy current coil at a constant distance from the surface of the tube being inspected.

6. The eddy current roller head of claim 5, wherein said means for centering said main body portion comprises whisker wheels rotatably mounted thereon.

7. The eddy current roller head of claim 5, wherein said means for causing said roller housing to track the inner surface of the tube being inspected comprises opposing magnets mounted in said main body portion and said roller housing.

8. The eddy current roller head of claim 5, wherein said means for maintaining said eddy current coil at a constant distance from the tube surface comprises said coil holder being pivotally mounted in an offset manner and having its trailing edge biased outwardly toward the surface of the tube being inspected.

9. A rotating eddy current roller head for inspecting tubing, comprising:
   a. a main body portion;
   b. at least one whisker wheel rotatably mounted adjacent each end of said main body portion and sized to cause said main body portion to be centered in said tubing;
   c. a roller housing slidably mounted in said main body portion for radial movement relative thereto;
   d. opposing magnets mounted in said main body portion and said roller housing for biasing said roller housing outward and causing it to track the inner surface of the tube being inspected;
   e. a coil holder pivotally mounted in an offset manner at the exterior end of said roller housing on an axis of rotation substantially parallel to the longitudinal axis of said main body portion;
   f. an eddy current coil mounted in said coil holder; and
   g. means in said roller housing for maintaining said eddy current coil at a constant distance from the surface of the tube being inspected.

10. The eddy current roller head of claim 9, wherein said means for maintaining said eddy current coil at a constant distance from the tube surface comprises a spring mounted in said roller housing which biases the trailing edge of said coil holder toward the surface of the tube being inspected.

11. The eddy current roller head of claim 9, further comprising a roller mounted on said roller housing on either side of said coil holder.

* * * * *